United States Patent
Indo et al.

(10) Patent No.: US 9,453,408 B2
(45) Date of Patent: *Sep. 27, 2016

(54) SYSTEM AND METHOD FOR ESTIMATING OIL FORMATION VOLUME FACTOR DOWNHOLE

(71) Applicant: Schlumberger Technology Corporation, Sugar Land, TX (US)

(72) Inventors: Kentaro Indo, Sugar Land, TX (US); Kai Hsu, Sugar Land, TX (US); Julian Pop, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,718

(22) Filed: Aug. 17, 2015

(65) Prior Publication Data

US 2015/0354353 A1 Dec. 10, 2015

Related U.S. Application Data

(63) Continuation of application No. 13/913,462, filed on Jun. 9, 2013, now Pat. No. 9,109,434.

(51) Int. Cl.
 *G01J 3/28* (2006.01)
 *E21B 47/10* (2012.01)
 *G01V 8/10* (2006.01)
 (Continued)

(52) U.S. Cl.
 CPC ........... *E21B 47/102* (2013.01); *E21B 49/088* (2013.01); *G01N 21/31* (2013.01); *G01V 8/10* (2013.01)

(58) Field of Classification Search
 CPC ............... G01J 3/02; G01J 3/10; G01J 3/28; G01J 3/18; G01J 3/2803; G01J 3/2823
 See application file for complete search history.

(56) References Cited

U.S. PATENT DOCUMENTS

| | | |
|---|---|---|
| 6,350,986 B1 | 2/2002 | Mullins et al. |
| 7,336,356 B2 | 2/2008 | Vannuffelen et al. |
| 7,379,180 B2 | 5/2008 | Vannuffelen et al. |

(Continued)

FOREIGN PATENT DOCUMENTS

| | | |
|---|---|---|
| WO | 2012108886 A1 | 8/2012 |
| WO | 2014003840 A1 | 1/2014 |

OTHER PUBLICATIONS

Dong, et al., "New Downhole Fluid Analysis Tool for Improved Reservoir Characterization", SPE 108566—Offshore Europe, Aberdeen, Scotland, UK, Dec. 2008, pp. 1107-1116.

(Continued)

*Primary Examiner* — Abullahi Nur
(74) *Attorney, Agent, or Firm* — Kenneth L. Kincaid (57) ABSTRACT

A system includes a downhole formation fluid sampling tool and a processor. An optical spectrometer of the downhole formation fluid sampling tool is able to measure an optical characteristic of a formation fluid flowing through the downhole formation fluid sampling tool over a plurality of wavelengths. The optical spectrometer generates optical spectra data indicative of this optical characteristic. The processor is designed to receive the optical spectra data generated by the optical spectrometer and to estimate a formation volume factor of the formation fluid based on the optical spectra data.

18 Claims, 6 Drawing Sheets

(51) Int. Cl.
*E21B 49/08* (2006.01)
*G01N 21/31* (2006.01)

(56) References Cited

U.S. PATENT DOCUMENTS

| | | | |
|---|---|---|---|
| 7,428,925 | B2 | 9/2008 | Brown et al. |
| 7,644,610 | B2 | 1/2010 | Meister |
| 7,966,273 | B2 | 6/2011 | Hegeman et al. |
| 7,996,153 | B2 | 8/2011 | Niemeyer et al. |
| 8,024,125 | B2 | 9/2011 | Hsu et al. |
| 8,068,226 | B2 | 11/2011 | Csutak |
| 8,146,415 | B2 | 4/2012 | Cartellieri |
| 9,109,434 | B2 * | 8/2015 | Indo .................. E21B 47/102 |
| 2003/0062472 | A1 | 4/2003 | Mullins et al. |
| 2004/0218176 | A1 | 11/2004 | Shammal et al. |
| 2004/0233446 | A1 | 11/2004 | Dong et al. |
| 2005/0007583 | A1 * | 1/2005 | DiFoggio .................. G01V 8/02 356/301 |
| 2006/0155474 | A1 | 7/2006 | Venkataramanan et al. |
| 2008/0066537 | A1 | 3/2008 | Hegeman et al. |
| 2010/0192684 | A1 | 8/2010 | Wu et al. |
| 2011/0048700 | A1 | 3/2011 | van Zuilekom et al. |
| 2011/0087459 | A1 | 4/2011 | Zazovsky et al. |
| 2011/0088895 | A1 | 4/2011 | Pop et al. |
| 2011/0218736 | A1 | 9/2011 | Pelletier |
| 2012/0018152 | A1 | 1/2012 | Zuilekom et al. |
| 2013/0118734 | A1 | 5/2013 | Csutak |
| 2014/0096955 | A1 | 4/2014 | Indo et al. |

OTHER PUBLICATIONS

Fujisawa, et al., "Analyzing Reservoir Fluid Composition In-Situ in Real Time: Case Study in a Carbonate Reservoir", SPE 84092—SPE Annual Technical Conference and Exhibition, Denver, Colorado, Oct. 5-8, 2003, pp. 1-9.

Hegeman, et al., "Application of Artificial Neural Networks to Downhole Fluid Analysis", SPE 123423—SPE Reservoir Evaluation & Engineering, vol. 12 (1), 2009, pp. 8-13.

International Search Report and Written Opinion issued in PCT/US2014/041369 on Sep. 29, 2014, 14 pages.

International Search Report and Written Opinion issued in PCT/US2013/063072 on Jan. 7, 2014, 11 pages.

Mullins, et al., "First Observation of the Urbach Tail in a Multicomponent Organic System", Applied Spectroscopy, vol. 46 (2), 1992, pp. 354-356.

Mullins, et al., "The Electronic Absorption Edge of Petroleum", Applied Spectroscopy, vol. 6 (9), 1992, pp. 1405-1411.

Smits, A.R., "In-Situ Optical Fluid Analysis as an Aid to Wireline Formation Sampling", SPE Formation Evaluation, vol. 10 (2), Jun. 1995, pp. 91-98.

Vazquez, et al., "Correlations for Fluid Physical Property Prediction", SPE 6719—Journal of Petroleum Technology, vol. 32 (6), 1980, pp. 968-970.

Venkataramanan, et al., "Downhole Fluid Analysis and Fluid Comparison Algorithm as an Aid to Reservoir Characterization", SPE 100937—SPE Asia Pacific Oil & Gas Conference and Exhibition, Adelaide, Australia, Dec. 11-13, 2006, pp. 1-16.

\* cited by examiner

SYSTEM AND METHOD FOR ESTIMATING OIL FORMATION VOLUME FACTOR DOWNHOLE

CROSS-REFERENCE TO RELATED APPLICATION

This application is a continuation of co-pending U.S. patent application Ser. No. 13/913,462, filed Jun. 9, 2013, which is herein incorporated by reference.

BACKGROUND

The present disclosure relates generally to drilling systems and more particularly to tools for sampling and analyzing formation fluid.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Wells are generally drilled into a surface (land-based) location or ocean bed to recover natural deposits of oil and gas, as well as other natural resources that are trapped in geological formations in the Earth's crust. A well is often drilled using a drill bit attached to the lower end of a drill string, which includes drillpipe, a bottom hole assembly, and other components that facilitate turning the drill bit to create a borehole. Drilling fluid, or "mud," is pumped down through the drill string to the drill bit during a drilling operation. The drilling fluid lubricates and cools the drill bit, and it carries drill cuttings back to the surface in an annulus between the drill string and the borehole wall.

Information about the subsurface formations, such as measurements of the formation pressure, formation permeability, and recovery of formation fluid samples, may be useful for predicting the economic value, the production capacity, and production lifetime of a subsurface formation. Downhole tools, such as formation testers, may perform evaluations in real-time during sampling of the formation fluid.

When evaluating subsurface formations containing crude oil, a measurement of oil formation volume factor may be useful for appraising the formation. Formation volume factor is defined as a volume ratio of the crude oil at reservoir conditions to the oil at its stock tank condition. Stock tank oil condition represents a standard temperature and pressure condition (e.g., 25 t and 1 atm). Formation volume factor may be used to estimate an amount of liquid oil within the reservoir. Typically, samples of formation fluid are brought to the surface for laboratory evaluation, and PVT analysis of the sample yields a measure of formation volume factor.

SUMMARY

In a first embodiment, a system includes a downhole formation fluid sampling tool and a processor. An optical spectrometer of the downhole formation fluid sampling tool is able to measure an optical characteristic of a formation fluid flowing through the downhole formation fluid sampling tool over a plurality of wavelengths. The optical spectrometer acquires optical spectra data indicative of this optical characteristic. The processor is designed to receive the optical spectra data acquired by the optical spectrometer and to estimate a formation volume factor of the formation fluid based on the optical spectra data.

In another embodiment, a method includes receiving optical spectra data into a processor. The optical spectra data is representative of optical characteristics of a formation fluid flowing through a downhole formation fluid sampling tool. The method also includes estimating, using the processor, a formation volume factor of the formation fluid based on the optical spectra data.

In a further embodiment, a method includes receiving formation fluid data into a processor. The formation fluid data is representative of characteristics of a formation fluid flowing through a downhole formation fluid sampling tool. The method also includes estimating, via the processor, a formation volume factor of the formation fluid based on the formation fluid data. This estimation is performed while the downhole formation fluid sampling tool is disposed within a wellbore extending into a formation.

Various refinements of the features noted above may exist in relation to various aspects of the present disclosure. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions can be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Present embodiments are directed to systems and methods for estimating an oil formation volume factor of a formation fluid using optical spectra data obtained from a spectrometer in a formation fluid sampling tool configured for operation downhole. The estimation may involve estimating various parameters from the optical spectra data, and combining these parameters according to a particular relationship. These parameters may include, for example, formation fluid composition and de-colored optical spectra data, among others. The estimation may be performed during sampling of the formation fluid, without employing time-consuming pressure/volume/temperature (PVT) analyses on the formation fluid. The estimation may allow an operator to make informed and time efficient decisions about a formation fluid based on the estimated formation volume factor.

Figure 1:
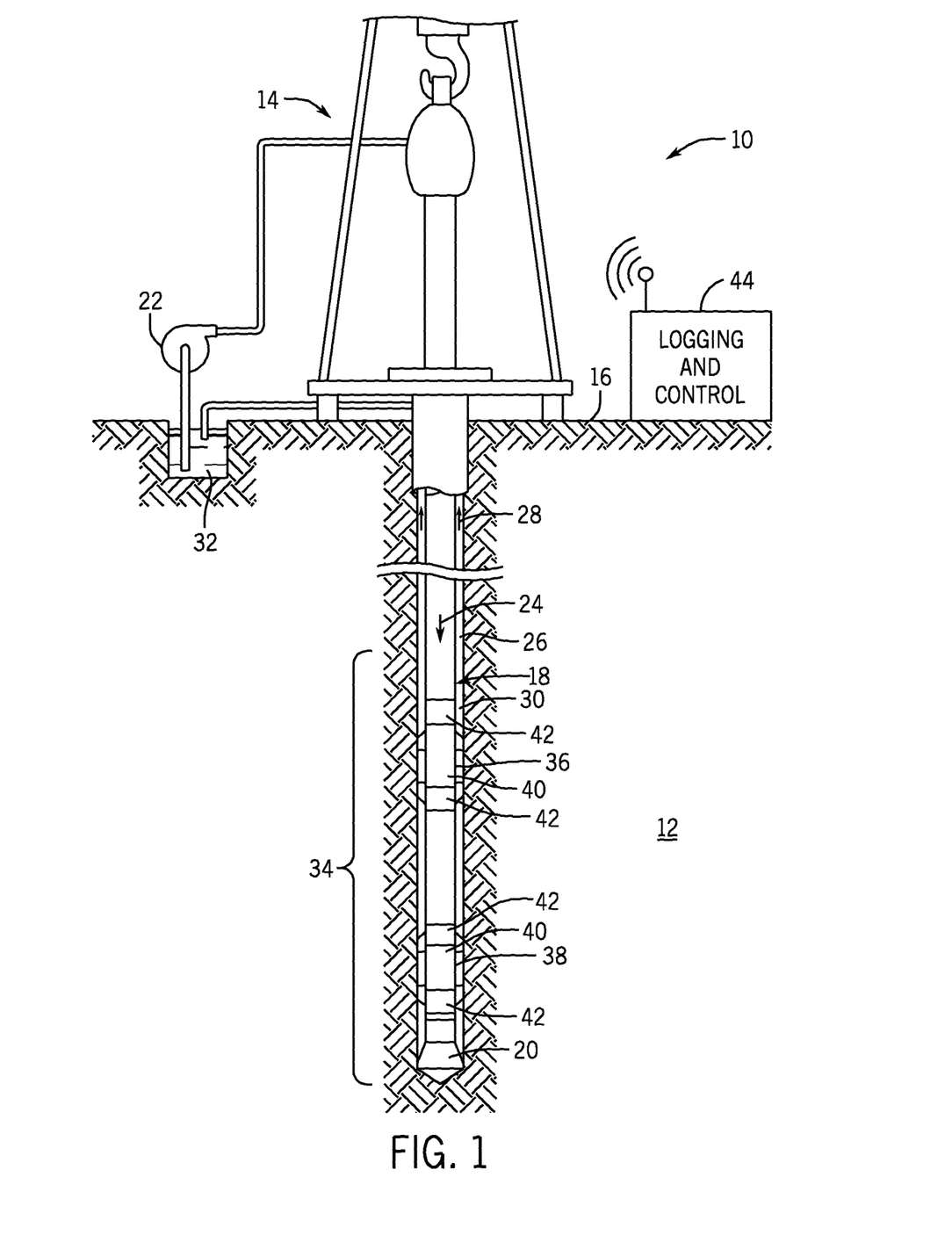
FIG. 1 is a schematic representation including a partial cross sectional view of a drilling system used to drill a well through subsurface formations, in accordance with an embodiment of the present techniques.

FIG. 1 illustrates a drilling system 10 used to drill a well through subsurface formations 12. A drilling rig 14 at the surface 16 is used to rotate a drill string 18 that includes a drill bit 20 at its lower end. As the drill bit 20 is rotated, a "mud" pump 22 is used to pump drilling fluid, commonly referred to as "mud" or "drilling mud," downward through the center of the drill string 18 in the direction of the arrow 24 to the drill bit 20. The mud, which is used to cool and lubricate the drill bit 20, exits the drill string 18 through ports (not shown) in the drill bit 20. The mud then carries drill cuttings away from the bottom of a wellbore 26 as it flows back to the surface 16, as shown by the arrows 28 through an annulus 30 between the drill string 18 and the formation 12. At the surface 16, the return mud is filtered and conveyed back to a mud pit 32 for reuse.

While a drill string 18 is illustrated in FIG. 1, it will be understood that the embodiments described herein are applicable to work strings and wireline tools as well. Work strings may include a length of tubing (e.g. coil tubing) lowered into the well for conveying well treatments or well servicing equipment. Wireline tools may include formation testing tools suspended from a multi-wire cable as the cable is lowered into a well so that it can measured formation properties at desired depths. It should be noted that the location and environment of the well may vary widely depending on the formation 12 into which it is drilled. Instead of being a surface operation, for example, the well may be formed under water of varying depths, such as on an ocean bottom surface. Certain components of the drilling system 10 may be specially adapted for underwater wells in such instances.

As illustrated in FIG. 1, the lower end of the drill string 18 includes a bottom-hole assembly ("BHA") 34 that includes the drill bit 20, as well as a plurality of drill collars 36, 38. The drill collars 36, 38 may include various instruments, such as sample-while-drilling ("SWD") tools that include sensors, telemetry equipment, and so forth. For example, the drill collars 36, 38 may include logging-while-drilling ("LWD") modules 40 and/or measurement-while drilling ("MWD") modules 42. The LWD modules or tools 40 may include tools configured to measure formation parameters or properties, such as resistivity, porosity, permeability, sonic velocity, and so forth. The MWD modules or tools 42 may include tools configured to measure wellbore trajectory, borehole temperature, borehole pressure, and so forth. The LWD modules 40 of FIG. 1 are each housed in one of the drill collars 36, 38, and each contain any number of logging tools and/or fluid sampling devices. The LWD modules 40 include capabilities for measuring, processing and/or storing information, as well as for communicating with the MWD modules 42 and/or directly with the surface equipment such as, for example, a logging and control unit 44. That is, in some embodiments, the SWD tools (e.g., LWD and MWD modules 40, 42) may be communicatively coupled to the logging and control unit 44 disposed at the surface 16. In other embodiments, portions of the logging and control unit 44 may be integrated with downhole features.

The LWD modules 40 and/or the MWD modules 42 may include a downhole fluid formation sampling tool configured to sample formation fluid. In presently disclosed embodiments, the drilling system 10 may be capable of estimating certain properties associated with the sampled formation fluid. These properties may include an estimated oil formation volume factor of the formation fluid. This and other estimated properties may be determined within or communicated to the logging and control unit 44, and used as inputs to various control functions and/or data logs. The formation volume factor may be used to calculate oil in place (OIP) of the formation:

$$OIP = \frac{V_{rock}\phi(1 - S_w)}{B_o} \qquad (1)$$

In equation 1, $V_{rock}$ is a bulk volume of the reservoir rock, which can be determined through seismic measurements performed via vertical seismic profile (VSP), or from surface seismics. In addition, $\phi$ represents the porosity of the formation, which can also be determined downhole via neutron, density, or nuclear magnetic resonance (NMR) measurements. Similarly, $S_w$ represents water saturation of the formation fluid, which may be determined via a downhole formation resistivity measurement. Presently disclosed embodiments allow for the estimation of formation volume factor ($B_o$) based on optical spectrometer measurements performed via the LWD 40 as well, so that an initial prediction of the OIP may be determined without bringing the formation sample to the surface for testing, and without time-consuming laboratory PVT processes.

Figure 2:
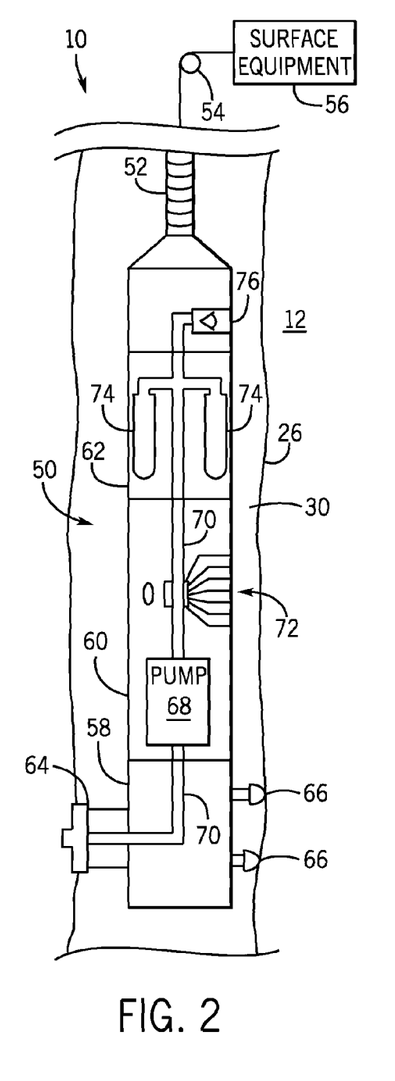
FIG. 2 is a schematic diagram of downhole equipment used to sample a subsurface formation, in accordance with an embodiment of the present techniques.

FIG. 2 is a schematic diagram of an embodiment of downhole equipment (equipment configured for operation downhole) used to sample a well formation. Specifically, the illustrated downhole equipment includes an embodiment of a downhole fluid formation sampling tool 50, hereinafter referred to as a downhole tool 50. The downhole tool 50 is illustrated as being disposed within the wellbore 26 of the subsurface formation 12 in order to sample formation fluid from the formation 12. In the illustrated embodiment, the downhole tool 50 is disposed in the wellbore 26 via a wireline 52. The downhole tool 50 may be suspended in the wellbore 26 from a lower end of the wireline 52, which may be a multi-conductor cable spooled, from a winch 54. The wireline 52 may be electrically coupled to surface equipment 56, in order to communicate various control signals and logging information between the downhole tool 50 and the surface equipment 56. It should be noted that in other embodiments, such as shown in FIG. 1, the downhole tool 50 may include one or more of the SWD tools, which are disposed in the wellbore 26 via the drill string 18.

The illustrated downhole tool 50 includes a probe module 58, a pumpout module 60, and a multi-sample module 62. It should be noted that other arrangements of the modules that make up the downhole tool 50 may be possible. Moreover, the different components shown within each of the illustrated modules may be arranged differently in other embodiments of the downhole tool 50.

The illustrated probe module 58 includes an extendable fluid communication line (probe 64) designed to engage the formation 12 and to communicate fluid samples from the formation 12 into the downhole tool 50. In addition to the probe 64, the illustrated probe module 58 includes two setting mechanisms 66. The setting mechanisms 66 may include pistons in some embodiments, although other types of probe modules 58 may utilize a different type of probe 64 and/or setting mechanism 66. For example, in some embodiments the probe module 58 may include one or more packer elements (not shown) configured to be inflated to contact an inner wall of the wellbore 26, thereby isolating a section of the wellbore 26 for sampling. In addition, the probe module 58 may include electronics, batteries, sensors, and/or hydraulic components used to operate the probe 64 and the corresponding setting mechanisms 66.

The pumpout module 60 may include a pump 68 used to create a pressure differential that draws the formation fluid in through the probe 64 and pushes the fluid through a flowline 70 of the downhole tool 50. The pump 68 may include an electromechanical pump used for pumping formation fluid from the probe module 58 to the multi-sample module 62 and/or out of the downhole tool 50. In an embodiment, the pump 68 operates as a piston displacement unit (DU) driven by a ball screw coupled to a gearbox and an electric motor, although other types of pumps 68 may be possible as well. Power may be supplied to the pump 68 via other components located in the pumpout module 60, or via a separate power generation module (not shown). During a sampling period, the pump 68 moves the formation fluid through the flowline 70, toward the multi-sample module 62.

In addition to the pump 68, the illustrated pumpout module 60 includes an optical spectrometer 72 configured to measure an optical characteristic of the formation fluid as it flows through the flowline 70 toward the multi-sample module 62. In the illustrated embodiment, the optical spectrometer 72 is located downstream of the pump 68, although in other embodiments the optical spectrometer 72 may be located upstream of the pump 68. The optical characteristic sensed by the spectrometer 72 may include optical density of the formation fluid, or any other desirable optical characteristic. Optical data collected via the spectrometer 72 may be used to control the downhole tool 50. For example, the downhole tool 50 may not operate in a sampling mode until the formation fluid flowing through the flowline 70 exhibits optical characteristics of a clean formation fluid sample, as detected by the spectrometer 72. A clean formation fluid sample contains a relatively low level of contaminants (e.g., drilling mud filtrate) that are miscible with the formation fluid when extracted from the formation.

The multi-sample module 62 includes one or more sample bottles 74 for collecting samples of the formation fluid. Based on the optical density, or other sensed characteristics, of the formation fluid detected via sensors (e.g., spectrometer 72) along the flowline 70, the downhole tool 50 may be operated in a sampling mode or a continuous pumping mode. When operated in the sampling mode, valves (not shown) disposed at or near entrances of the sample bottles 74 may be positioned to allow the formation fluid to flow into the sample bottles 74. The sample bottles 74 may be filled one at a time, and once a sample bottle 74 is filled, its corresponding valve may be moved to another position to seal the sample bottle 74. When the valves are closed, the downhole tool 50 may operate in a continuous pumping mode.

In a continuous pumping mode, the pump 68 moves the formation fluid into the downhole tool 50 through the probe 64, through the flowline 70, and out of the downhole tool 50 through an exit port 76. The exit port 76 may be a check valve that releases the formation fluid into the annulus 30 of the wellbore 26. The downhole tool 50 may operate in the continuous pumping mode until the formation fluid flowing through the flowline 70 is determined to be clean enough for sampling. This is because when the formation fluid is first sampled, drilling mud filtrate that invades into the formation may enter the downhole tool 50 along with the sampled formation fluid. After pumping the formation fluid for an amount of time, the formation fluid flowing through the downhole tool 50 will provide a cleaner fluid sample of the formation 12 than would otherwise be available when first drawing fluid in through the probe 64. The formation fluid may be considered clean when the optical spectra data from the spectrometer 72 indicates that the formation fluid contains less than approximately 1%, 5%, or 10% filtrate contamination (by volume).

Figure 3:
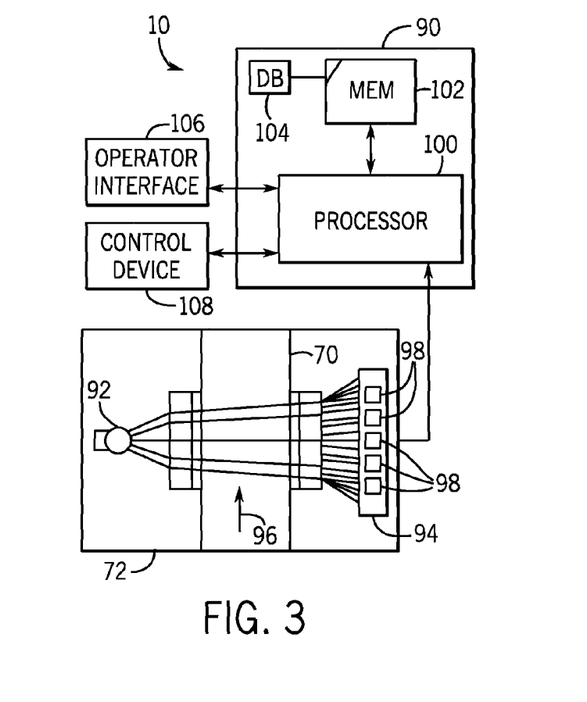
FIG. 3 is a schematic diagram of equipment used to predict formation fluid properties of formation fluid flowing through the downhole equipment of FIG. 2, in accordance with an embodiment of the present techniques.

The optical characteristics of the formation fluid measured by the spectrometer 72 may be useful for performing a variety of evaluation and control functions, in addition to determining when the formation fluid flowing through the flowline 70 is relatively clean for sampling. For example, the data collected from the spectrometer may be used to estimate formation volume factor of the formation fluid. FIG. 3 is a schematic diagram of equipment that may be used in the drilling system 10 to predict the formation fluid properties. Such equipment, in the illustrated embodiment, includes the spectrometer 72 and a control/monitoring system 90.

The spectrometer 72 is shown in detail in the illustrated embodiment. The spectrometer 72 may include a light source 92 and a detector 94 disposed on opposite sides of the flowline 70 through which the formation fluid flows, as indicated by arrow 96. The spectrometer 72 may be part of the downhole tool 50, and may be located along any portion of the flowline 70 that directs the formation fluid through the downhole tool 50. Although a single light source 92 is shown, other embodiments of the spectrometer 72 may include additional light sources 92. The detector 94 may sense the light that passes through the formation fluid in the flowline 70.

The detector 94 may include one or more detector elements 98, each detector element 98 is designed to measure the amount of light transmitted at a certain wavelength. For example, the detector elements 98 may detect the light transmitted from the visible to near-infrared within a range of 1, 5, 10, 20, or more different wavelengths approximately from 400 to 2200 nm. However, other numbers of wavelengths (corresponding to the number of detector elements) and other ranges of wavelengths may be possible. For example, in some embodiments it may be desirable to detect optical characteristics of the formation fluid at a relatively limited range of wavelengths, such as the near infrared (NIR) wavelength range of approximately 800-2500 nm, 1500-2050 nm, or 1600-1800 nm. Estimations of the formation volume factor of the formation fluid may be performed using optical data collected at a single wavelength, or at multiple wavelengths.

The spectrometer 72 may measure certain optical characteristics of the formation fluid flowing through the flowline 70, and output optical spectra data representative of the detected optical characteristics. In an embodiment, the optical characteristics may include optical density of the formation fluid at each of the detected wavelengths. Optical density is a logarithmic measurement relating the intensity of light emitted from the light source 92 to the intensity of light detected by the detector 94 at a certain wavelength. Optical density may be expressed according to the equation shown below:

$$OD_\lambda = -\log\left\{\frac{I}{I_o}\right\} \quad (2)$$

In equation 2, $I_o$ represents the light intensity emitted from the light source 92, and I represents the light intensity measured by the detector element 98 corresponding to the particular wavelength λ. When expressed in this manner, a measured optical density (OD) of 0 corresponds to 100% of light transmission through the formation fluid at that wavelength. Similarly, an OD of 1 corresponds to 10% light transmission through the formation fluid, and an OD of 2 corresponds to 1% light transmission. The higher the optical density of the formation fluid, the lower the amount of light that is transmitted through the formation fluid and detected by the detector 94.

The spectrometer 72 may send optical spectra data representative of the measured optical characteristics to a processor 100 of the control/monitoring system 90. The term "processor" refers to any number of processor components located about the drilling system 10. In some embodiments, for example, the processor 100 may include a single processor disposed onboard the downhole tool 50. In other embodiments, the processor 100 may be located within the surface equipment 56 of FIG. 2, or the logging and control unit 44 of FIG. 1. In still further embodiments, the processor 100 may include one or more processors located within the downhole tool 50 connected to one or more processors located in drilling equipment disposed at the surface 16 of the drilling system 10. Moreover, any desirable combination of processors may be considered part of the processor 100 in the following discussion. Similar terminology is applied with respect to the control/monitoring system 90 as well as a memory 102 of the control/monitoring system 90, meaning that the control/monitoring system 90 may include any number of processors communicatively coupled to each other and to memories located throughout the drilling system 10.

The control/monitoring system 90 may estimate the formation volume factor of the formation fluid based on the optical spectra data received from the spectrometer 72. To make this calculation, as well as other estimations, the processor 100 may execute instructions stored in the memory 102.

In some embodiments, the processor 100 may utilize one or more datasets stored in a database 104 within the memory 102. Such datasets may include a record of optical spectra data and corresponding parameters (e.g., composition, formation volume factor, de-colored optical spectrum) of the formation fluid taken via prior formation fluid sampling using the downhole tool 50. The formation fluid parameters stored in the dataset may include results from laboratory tests performed on formation fluid previously sampled by the downhole tool 50. In some embodiments, the processor 100 may use information derived from the dataset to estimate the formation volume factor based on expected results for the optical spectra data from prior formation fluid samples in the database. As more samples are taken using the downhole tool 50, the datasets may be updated within the database 104 to include more information for performing the estimations.

The processor 100 may be communicatively coupled with one or more operator interfaces 106 and/or control devices 108. The operator interface 106 may include logs of predicted formation fluid properties that are accessible to an operator. The control device 108 may include any device or portion of the drilling system 10 that receives control signals for operation based on the estimated properties (e.g., formation volume factor) of the formation fluid. Such control devices 108 may implement changes in depth of the downhole tool 50 within the wellbore 26, adjustments to the pumping pressure of the pump 68, and/or other control functions, based on the estimated formation fluid properties.

Having now discussed a general physical setup of drilling system components that may facilitate substantially real-time estimation of formation volume factor of the formation fluid, a detailed discussion of one possible derivation of oil formation volume factor is provided. Specifically, the derivation outlines an estimation of oil formation volume factor (FVF) based in part on optical density of the formation fluid across one or more wavelengths. Optical absorbance (e.g., optical spectra data) of the formation fluid may be defined using Beer-Lambert's approximation given below:

$$\Omega = \varepsilon \cdot c \cdot l = \varepsilon \cdot \frac{M}{V} \cdot l \quad (3)$$

In equation 3, Ω represents the optical spectra of a medium (e.g., formation fluid), ε represents an absorption coefficient of the medium, c represents a concentration of the medium, l represents an optical pathlength, M represents the mass of the medium, and V represents the volume of the medium. As noted above, FVF is a volumetric ratio of crude oil at formation condition (i.e., live oil) $V_{LO}$ to its stock tank oil $V_{STO}$ at the surface 16. This live oil may represent the formation fluid in the formation or as it flows through the downhole tool 50, while the downhole tool 50 is disposed within the wellbore 26. The stock tank oil may represent the formation fluid at a surface condition of approximately 60° F. and approximately 14.7 psia. The optical density of the stock tank oil at this standard condition may be expressed as follows:

$$\Omega_{STO} = \varepsilon_{STO} \cdot c_{STO} \cdot l = \varepsilon_{STO} \cdot \frac{M_{STO}}{V_{STO}} \cdot l \tag{4}$$

Equation 4 represents the application of equation 3 to the stock tank oil medium (i.e. STO).

The optical density of the live oil at a particular temperature and pressure is defined as a linear combination of the optical spectra of its STO at the live oil condition and the optical spectra of its gas components at the live oil condition. Optical spectra of the STO at the live oil condition is provided below:

$$\Omega'_{STO.} = \varepsilon_{STO} \cdot c'_{STO} \cdot l = \varepsilon_{STO} \cdot \frac{M_{STO}}{V_{L.O.}} \cdot l \tag{5}$$

In equation 5, $c'_{STO}$ represents the concentration of the stock tank oil at the live oil temperature and pressure. The concentration is defined as the mass of the stock tank oil divided by the volume of the live oil. It should be noted that the spectrum of STO at the live oil condition differs from the spectrum of STO at the stock tank oil condition. Specifically, the concentration differs due to a volume expansion of the STO.

Optical spectra of the gas component of the live oil is provided below:

$$\Omega_{gas.} = \sum_i \varepsilon_i \cdot (\mu_i \cdot c_i) \cdot l = \sum_i \varepsilon_i \cdot \frac{\mu_i \cdot M_i}{V_{L.O.}} \cdot l \tag{6}$$

In equation 6, the index i represents each of the multiple components that make up the formation fluid (in vapor phase). These components may include, for example, hydrocarbon groups such as methane (C1), ethane (C2), propane to pentane (C3-5), hexane and heavier hydrocarbons (C6+), and carbon dioxide (CO2). In equation 6, $\mu_i$ represents the vapor fraction of the component i.

As noted above, the optical spectrum of the live oil is a linear combination of equations 5 and 6:

$$\Omega_{L.O.} = \Omega'_{STO} + \Omega_{gas} = \varepsilon_{STO} \cdot c'_{STO} \cdot l + \sum_i \varepsilon_i \cdot (\mu_i \cdot c_i) \cdot l \tag{7}$$

$$= \left(\varepsilon_{STO} \cdot M_{STO} + \sum_i \varepsilon_i \cdot \mu_i \cdot M_i\right) \cdot \frac{l}{V_{L.O.}}$$

In equation 7, $\varepsilon_i$ is the absorption coefficient of component i (for i=C1, C2, C3-5, C6+ and CO2). Similarly, $c_i$ is the concentration of component i, $M_i$ is the mass of component i, and $\mu_i$ is the vapor fraction of component i.

Oil formation volume factor $B_o$ is the volume ratio of live oil at formation condition to STO at standard (STO) condition. As noted above, live oil is the oil (with gas) that comes directly from the formation and flows through the downhole tool 50. Stock tank oil is the corresponding oil that remains after the sampled formation fluid is brought to the surface and the gas, liberated under surface conditions, is removed from the sample. From equation 4, the STO volume is given as:

$$V_{STO} = \varepsilon_{STO} \cdot M_{STO} \cdot \frac{l}{\Omega_{STO}} \tag{8}$$

Likewise, equation 7 can be rearranged to provide the live oil volume:

$$V_{L.O.} = \left(\varepsilon_{STO} \cdot M_{STO} + \sum_i \varepsilon_i \cdot \mu_i \cdot M_i\right) \cdot \frac{l}{\Omega_{L.O.}} \tag{9}$$

Dividing equation 9 by equation 8 then yields the estimated oil formation volume factor:

$$B_o = \frac{V_{L.O.}}{V_{STO}} = \frac{\left(\varepsilon_{STO} \cdot M_{STO} + \sum_i \varepsilon_i \cdot \mu_i \cdot M_i\right) \cdot \frac{l}{\Omega_{L.O.}}}{\varepsilon_{STO} \cdot M_{STO} \cdot \frac{l}{\Omega_{STO}}} \tag{10}$$

$$= \frac{\Omega_{STO}}{\Omega_{L.O.}} \cdot \frac{\left(\varepsilon_{STO} \cdot M_{STO} + \sum_i \varepsilon_i \cdot \mu_i \cdot M_i\right)}{\varepsilon_{STO} \cdot M_{STO}}$$

$$= \frac{\Omega_{STO}}{\Omega_{L.O.}} \cdot \left(1 + \sum_i \tilde{\varepsilon}_i \cdot \mu_i \cdot \frac{M_i}{M_{STO}}\right)$$

In equation 10, $\tilde{\varepsilon}_i$ represents the absorption coefficient of the component i taken with respect to the absorption coefficient of the STO, as shown below:

$$\tilde{\varepsilon}_i = \frac{\varepsilon_i}{\varepsilon_{STO}} \tag{11}$$

In addition, the mass of the stock tank oil ($M_{STO}$ of equation 10) may be defined in terms of the individual component masses $M_i$ and the respective vapor fractions $\mu_i$, according to the following relationship:

$$M_{STO} = \sum_k (1 - \mu_k) M_k \tag{12}$$

In equation 12, k represents each of the following components of the formation fluid: k=C1, C2, C3-5, C6+, and CO2). Combining equations 10 and 12 yields the following:

$$B_o = \frac{\Omega_{STO}}{\Omega_{L.O.}} \cdot \left(1 + \sum_i \tilde{\varepsilon}_i \cdot \mu_i \cdot \frac{M_i}{M_{STO}}\right) \tag{13}$$

$$= \frac{\Omega_{STO}}{\Omega_{L.O.}} \cdot \left(1 + \sum_i \tilde{\varepsilon}_i \cdot \mu_i \cdot \frac{M_i}{\sum_k (1 - \mu_k) M_k}\right)$$

$$= \frac{\Omega_{STO}}{\Omega_{L.O.}} \cdot \left(1 + \sum_i \tilde{\varepsilon}_i \cdot \mu_i \cdot \frac{\frac{M_i}{V_{L.O.}}}{\sum_k (1 - \mu_k) \frac{M_k}{V_{L.O.}}}\right)$$

-continued $$= \frac{\Omega_{STO}}{\Omega_{L.O.}} \cdot \left(1 + \sum_i \tilde{\varepsilon}_i \cdot \mu_i \cdot \frac{\rho_i}{\sum_k (1-\mu_k)\rho_k}\right)$$

$$= \frac{\Omega_{STO}}{\Omega_{L.O.}} \cdot \left(1 + \sum_i \tilde{\varepsilon}_i \cdot \mu_i \cdot \frac{\tilde{\rho}_i}{\sum_k (1-\mu_k)\tilde{\rho}_k}\right)$$

The concentration $\tilde{\rho}_i$ in equation 13 represents a relative concentration of each component taken with respect to the concentration of C6+. This relative concentration may be calculated by comparing the weight fraction of each component with the weight fraction of C6+, as shown below:

$$\tilde{\rho}_i = \frac{\rho_i}{\rho_{C6+}} = \frac{w_i}{w_{C6+}} \quad (14)$$

At this point, certain assumptions can be made regarding variables that determine FVF. For example, the vapor fractions $\mu_i$ of C1, C2 and CO2 at standard (STO) condition are equal to one, and the absorption coefficient $\varepsilon_i$ of CO2 in the wavelength range of 1600 nm to 1800 nm is approximately equal to zero, or is negligible in comparison to the absorption coefficients of the hydrocarbons. Applying these two assumptions to equation 13 yields the following expression for estimating FVF:

$$B_o = \frac{\Omega_{STO}}{\Omega_{L.O.}} \cdot \left(1 + \frac{\tilde{\varepsilon}_{C1}\tilde{\rho}_{C1} + \tilde{\varepsilon}_{C2}\tilde{\rho}_{C2} + \tilde{\varepsilon}_{C3-5}\mu_{C3-5}\tilde{\rho}_{C3-5} + \tilde{\varepsilon}_{C6+}\mu_{C6+}}{(1-\mu_{C3-5})\tilde{\rho}_{C3-5} - \mu_{C6+} + 1}\right) \quad (15)$$

Again, $\tilde{\rho}_{C1}$, $\tilde{\rho}_{C2}$, and $\tilde{\rho}_{C3-5}$ can be calculated as a ratio of the weight fraction of each component C1, C2, and C3-5, to the weight fraction of C6+. The weight fractions w for each of the components may be calculated based on the composition of the formation fluid. The composition of the formation fluid may be estimated from the measured optical spectra data. The vapor fractions $\mu_{C3-5}$ and $\mu_{C6+}$ may also be determined based on the estimated composition of the formation fluid. The STO spectrum $\Omega_{STO}$ may be estimated after removing the spectral offset and scattering from the measured optical spectra data of a set of stock tank oil. That is, the $\Omega_{STO}$ value in equation 15 is a de-colored and de-scattered STO spectrum. The absorption coefficients $\tilde{\varepsilon}_{C1}$, $\tilde{\varepsilon}_{C2}$, $\tilde{\varepsilon}_{C3-5}$, and $\tilde{\varepsilon}_{C6+}$ generally depend on several different factors, including temperature, pressure, fluid composition, and so forth. However, the absorption coefficients may be assumed to be approximately constants, and these constants are obtained via an optimization procedure. The optimization procedure may be applied to a database of optical spectra data representing multiple formation fluid samples, as discussed in detail below.

Figure 4:
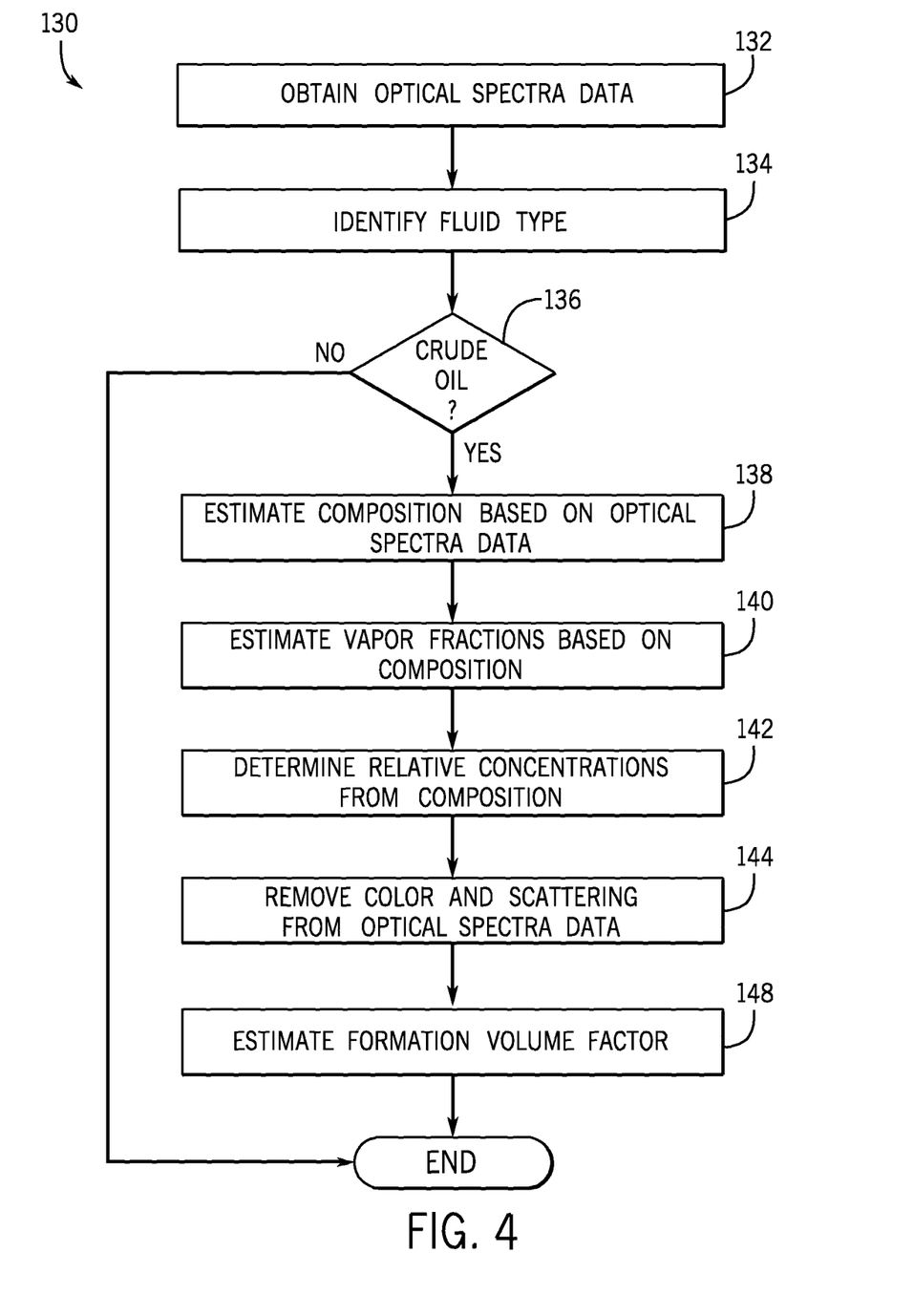
FIG. 4 is a process flow diagram of a method for estimating formation volume factor from optical spectra data received from an optical spectrometer, in accordance with an embodiment of the present techniques.

FIG. 4 is a process flow diagram of a method 130 for estimating the FVF of a formation fluid sampled via the downhole tool 50, while the downhole tool 50 is disposed in the wellbore 26. More specifically, the method 130 may be used to estimate the FVF based on optical spectra data generated by the spectrometer 72 onboard the downhole tool 50. It should be noted that the method 130 may be implemented as a computer or software program (e.g., code or instructions) that may be executed by the processor 100 to execute the method 130. Additionally, the program (e.g., code or instructions) may be stored in any suitable article of manufacture that includes at least one tangible non-transitory, computer-readable medium that at least collectively stores these instructions or routines, such as a memory (e.g., memory 102) or storage component of the control/monitoring system 90. The term non-transitory merely indicates that the medium is not a signal.

The method 130 includes obtaining (block 132) the optical spectra data from the spectrometer 72. The method 130 also includes identifying (block 134) a fluid type of the formation fluid based on the optical spectra data. The formation fluid may be, for example, a gas, gas condensate, or crude oil. Absorbance spectra (i.e., optical spectra data) of formation fluids generally include certain attributes indicative of the fluid type. For example, crude oils tend to feature a "tail", or series of peak levels of absorbance, in the near-infrared region of their optical spectrum. When detected, this tail functions as an indicator that the formation fluid being sampled is a crude oil. The processor 100 may be configured to analyze the optical spectra data for indicators such as this, to determine the formation fluid type. Additional details relating to identifying the formation fluid type are described in PCT Application Serial No. PCT/US2013/030637, entitled "METHOD AND APPARATUS FOR IDENTIFYING FLUID ATTRIBUTES," to Indo et al., filed on Mar. 13, 2013, with priority to Provisional Application No. 61/666,593, filed Jun. 29, 2012, which are incorporated into the present disclosure by reference. If the formation fluid is determined to be a crude oil (block 136), the process for estimating the FVF continues. However, if the formation fluid is determined to be a gas or gas condensate (i.e., not a crude oil), the method 130 ends since the procedure disclosed herein applies particularly to oils.

Upon determination that the formation fluid is a crude oil based on its optical spectra data, the method 130 includes estimating (block 138) a composition of the formation fluid based on the optical spectra data. This estimation may involve applying a calibration model to the detected optical spectra data. For example, the memory 102 may store a linear mapping matrix that maps the optical spectra data of crude oil to an expected composition of the formation fluid. This mapping matrix may be predetermined from a calibration dataset containing prior optical spectra data and corresponding composition values. Additional details relating to estimating the composition of the formation fluid from optical spectra data are described in U.S. patent application Ser. No. 13/644,772, entitled "DETERMINING FLUID COMPOSITION DOWNHOLE FROM OPTICAL SPECTRA," to Indo et al., filed on Oct. 4, 2012, which is incorporated into the present disclosure by reference. Any other available methods may be used to estimate (block 138) the composition from the optical spectra data.

Other measures may be derived from the estimated composition for use in estimating the FVF. For example, in an embodiment, the method 130 includes estimating (block 140) vapor fractions of multiple components of the formation fluid based on the estimated composition. According to equation 15, the vapor fractions may be determined for the components C3-5 and C6+, since those for C1, C2, and CO2 are assumed to be one. In some embodiments, an artificial neural network (ANN) model may be applied to estimate these vapor fractions. ANN models function as non-linear statistical data models. The ANN model may be developed and trained based on database values of crude oil composition and corresponding vapor fractions of the respective components. The processor 100 may apply the ANN algorithm to the estimated composition to determine the vapor fraction estimates. Additional details relating to applying an ANN model to determine formation fluid properties (e.g., vapor fractions) are described in U.S. Pat. No. 7,966,273, entitled "PREDICTING FORMATION FLUID PROPERTY THROUGH DOWNHOLE FLUID ANALYSIS USING ARTIFICIAL NEURAL NETWORK," to Hegeman et al., issued on Jun. 21, 2011, which is incorporated into the present disclosure by reference. Other methods (e.g., linear modeling) may be applied to the estimated composition to obtain an estimate of the vapor fractions in other embodiments.

The method 130 may further include determining (block 142) relative concentrations of certain components of the formation fluid, based on the estimated composition. In some embodiments, the composition may be determined initially in terms of the relative concentrations of each component taken with respect to the concentration of C6+. In other embodiments, however, the composition may be determined as weight fractions or some other ratio of component concentrations. The processor 100 may normalize such weight fractions via equation 14 to determine a desired relative concentration for each component of the formation fluid.

In addition, the method 130 includes removing (block 144) color and scattering from the optical spectra data. This may involve determining and removing a color effect and a spectral offset from the optical spectra data obtained via the spectrometer 72. One possible way to perform such de-coloring and de-scattering is described in detail below.

The method 130 includes estimating (block 148) the FVF based on the estimated composition of the formation fluid and based on the de-colored and de-scattered optical spectrum. In some embodiments, estimating (block 148) FVF may include providing the estimated vapor fractions, the estimated relative concentrations, and the de-colored and de-scattered optical spectrum as inputs to equation 15. In some embodiments, a different equation may be used to combine each of the components estimated or determined from the optical spectra data. Moreover, different models altogether may be used to perform this estimation of FVF based on the optical spectra data received from the spectrometer 72.

Equation 15 may include certain coefficients and values that are predetermined from database information. For example, equation 15 may already include the absorption coefficients ($\tilde{\epsilon}_{C1}$, $\tilde{\epsilon}_{C2}$, $\tilde{\epsilon}_{C3-5}$, and $\tilde{\epsilon}_{C6+}$) described above. These absorption coefficients may be obtained offline and stored in the memory 102 for use in estimating the FVF. In some embodiments, there may be multiple different sets of absorption coefficients ($\tilde{\epsilon}_{C1}$, $\tilde{\epsilon}_{C2}$, $\tilde{\epsilon}_{C3-5}$, and $\tilde{\epsilon}_{C6+}$), each set of absorption coefficients corresponding to a different wavelength of the optical spectra data. The appropriate set of absorption coefficients may be selected by the processor 100 for use in the FVF estimation. The absorption coefficients may be sample independent, so that they may be applied similarly to any number of samples of optical spectra data at the same wavelength. An average stock tank oil (STO) spectrum $\Omega_{STO}$ may be present in equation 15 as well, this STO spectrum being an average of the de-colored and de-scattered optical spectrum of stock tank oil. An example of the determination of this average STO spectrum is provided below.

Figure 5:
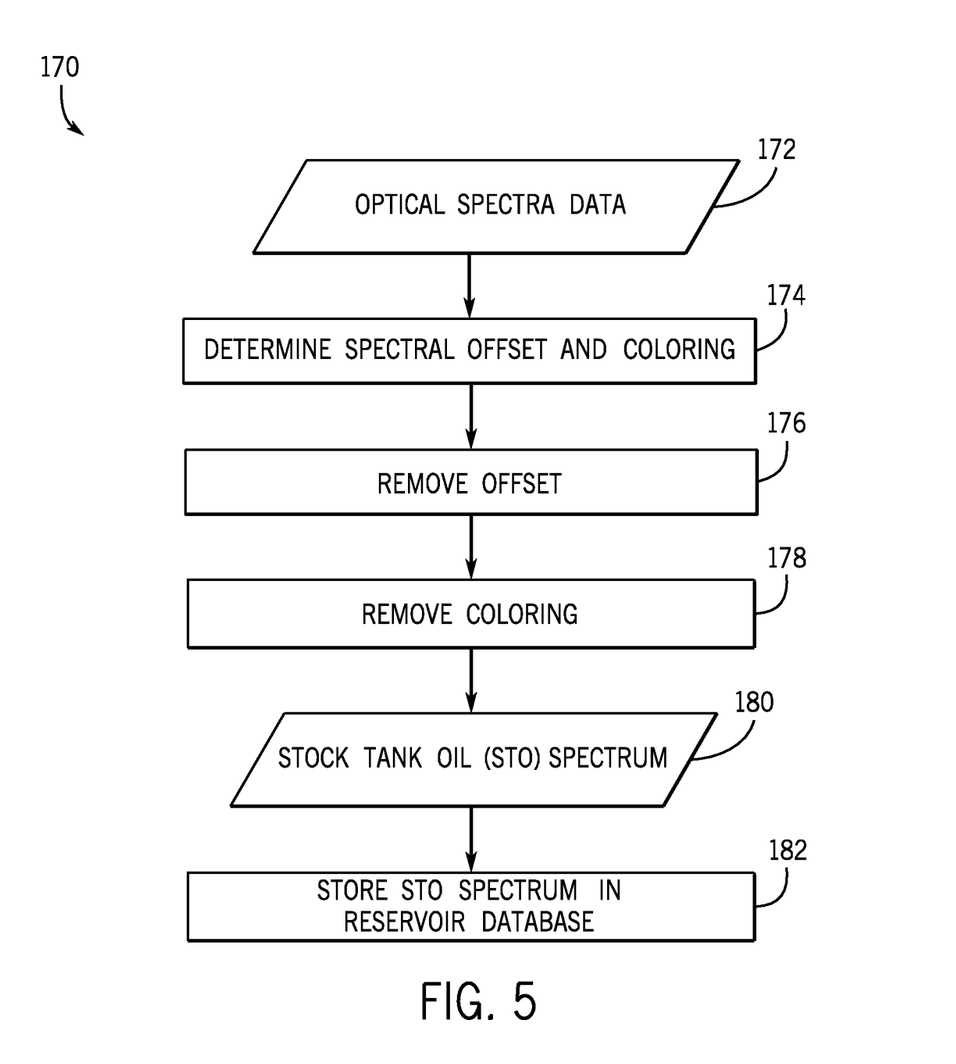
FIG. 5 is a process flow diagram of a method for estimating a stock tank oil spectrum based on optical spectra data of live oil, in accordance with an embodiment of the present techniques.

FIG. 5 is a process flow diagram of a method 170 for estimating the de-colored and de-scattered stock tank oil (STO) spectrum used in equation 15 for estimating the FVF. As noted above, the stock tank oil is a liquid portion of live oil at standard temperature and pressure conditions, and it does not contain gases (e.g., C1 and perhaps C2,) present in the live oil. The STO spectrum may be determined offline prior to performing the downhole fluid analysis that yields FVF. The STO spectrum may be an averaged value determined based on multiple sets of optical spectra data 172 of formation fluid at STO condition. This STO optical spectra data 172 may be stored in the database 104. In some embodiments, the database 104 may include live oil optical spectra data as well. The method 170 includes determining (block 174) a spectral offset and coloring present within the optical spectra data 172. The spectral offset (or scattering) is the same across the wavelengths of the optical spectra data 172, while the color effect may be different across the different wavelengths. Different samples of the optical spectra data 172 may be taken at different times, pressures, and/or temperatures relative to each other, but from the same formation 12.

The method 170 includes removing (block 176) the determined spectral offset (scattering) from each sample of the optical spectra data, and removing (block 178) the determined coloring contribution from each sample of the optical spectra data. Removing these components of the optical spectra data yields the estimated de-colored and de-scattered STO spectrum 180. This STO spectrum 180 may be stored in the memory 102 for use in the equation 15 during FVF estimation. In some embodiments, the estimated STO spectrum 180 of a single sample of optical spectra data may be used for FVF estimation. In other embodiments, multiple samples of the optical spectra data may be analyzed in the manner provided in method 170, and the resulting STO spectrum values may be averaged at each wavelength to estimate the STO spectrum 180 for use in the FVF estimation. In some embodiments, the method 170 may include storing (block 182) the STO spectra in a reservoir database (e.g., database 104). In such embodiments, the estimated FVF may be determined based on an average of the available STO spectra data stored in the database corresponding to the particular formation 12. A larger database of STO spectra data may yield a relatively more accurate estimation of the FVF. It should be noted that other methods for estimating STO spectrum may be utilized in other embodiments.

Figure 6:
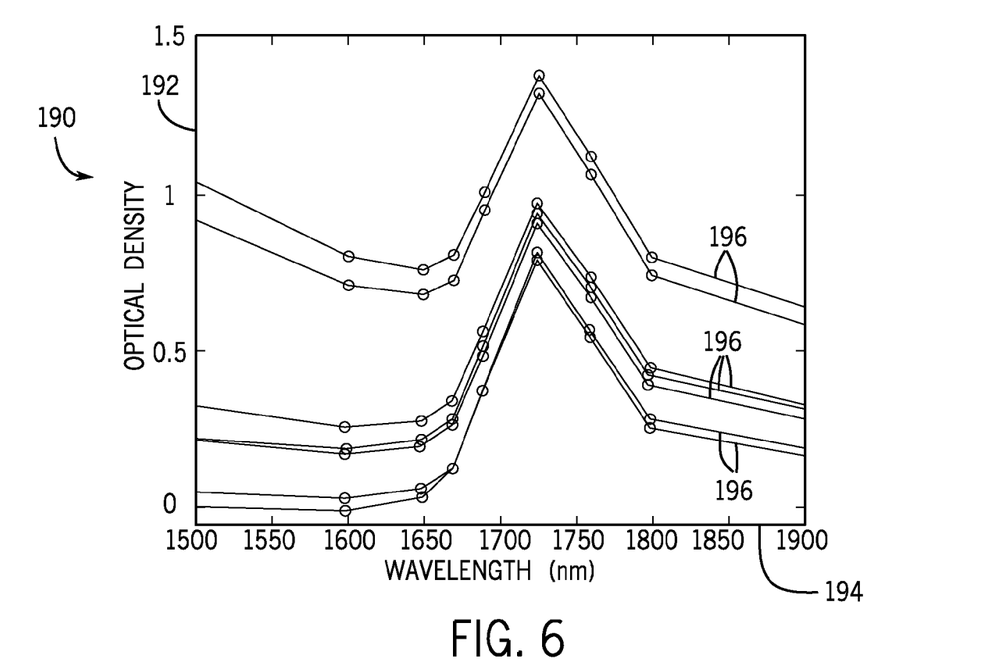
FIG. 6 is a plot illustrating optical spectra data of a crude oil across a near-infrared range of wavelengths, in accordance with an embodiment of the present techniques.
Figure 7:
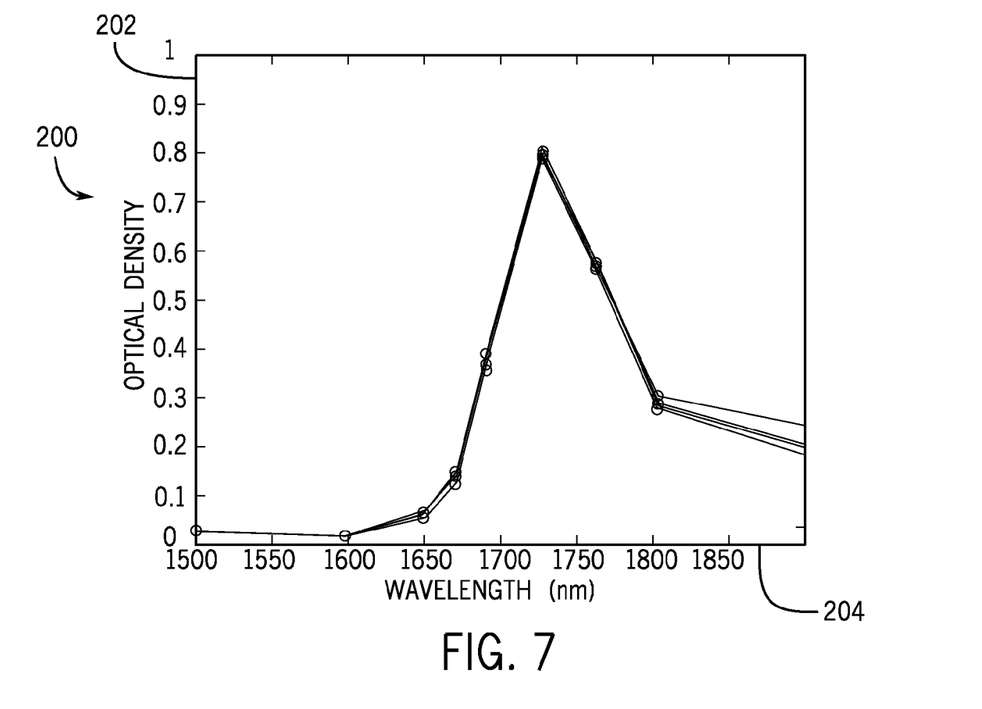
FIG. 7 is a plot illustrating de-colored optical spectra data corresponding to the optical spectra data of FIG. 6, in accordance with an embodiment of the present techniques.

FIGS. 6 and 7 illustrate the result of applying the method 170 to obtain de-colored and de-scattered STO spectra. Specifically, FIG. 6 is a plot 190 of optical density 192 taken across different wavelengths 194 within the near-infrared region. In the illustrated embodiment, seven different samples 196 of optical spectra data (i.e., stock tank oil spectra) are shown. The data samples 196 feature different vertical offsets due to the spectral offset present within each data sample 196. In addition, the data samples 196 have differing slopes at the lower wavelengths due to a "coloring" effect in the optical spectra data. The NIR tail region of the formation fluid optical spectrum, complete with scattering and any spectral offset, may be modeled as follows:

$$\Omega_{color+scat} = A \exp(E_a/\lambda) + B \qquad (16)$$

In equation 16, A and B are sample dependent, and $E_a$ is a universal value of approximately 4650 nm. In the method 170, determining (block 174) the spectral offset and the coloring in the optical spectra data may include determining the values of A and B in equation 16. In one embodiment, the optical density values at 1070 nm, 1290 nm, 1500 nm, and 1600 nm may be used to determine the parameters A and B. That is, each data sample 196 may be fitted to equation 16 to estimate the A and B values for that particular data sample 196. The lower wavelengths may be used in this determination since, at the higher wavelengths, the $\exp(E_a/\lambda)$ term goes to zero. Upon determining the spectral offset B and the coloring A, these offsets and coloring contributions may be removed from the optical spectra data to generate de-scattered and de-colored spectra, which represents the de-colored and de-scattered STO spectrum for each sample. The de-colored and de-scattered STO spectrum for the 5 samples may be averaged to yield the STO spectrum that is used in equation 15.

In other embodiments, different equations or methods may be used to determine coloring and the spectral offset in the NIR tail, besides the exponential function of equation 16. For example, other methods may include using a Gaussian distribution, an inverse gamma function, and so forth.

It should be noted that the same equation 16 and method for determining and removing the spectral offset (scattering) and the coloring may be applied to the live optical spectra data being analyzed to estimate the FVF. That is, equation 16 may be employed in the block 144 of the method 130 for removing the color and scattering from the obtained optical spectra data.

FIG. 7 is a plot 200 of optical density 202 with respect to wavelength 204 of the de-colored and de-scattered STO spectra corresponding to the optical spectra data shown in FIG. 6, after removing the color and scattering. In the illustrated embodiment, the optical spectra data samples 196 are aligned at 1600 nm. As shown in the illustrated embodiment, the optical spectra corresponding to the seven different data samples 196 are nearly overlapping across the different wavelengths 204. The average of these de-colored and de-scattered STO optical spectrum values may be taken at one or more wavelengths and used in equation 15 to estimate the FVF.

Figure 8:
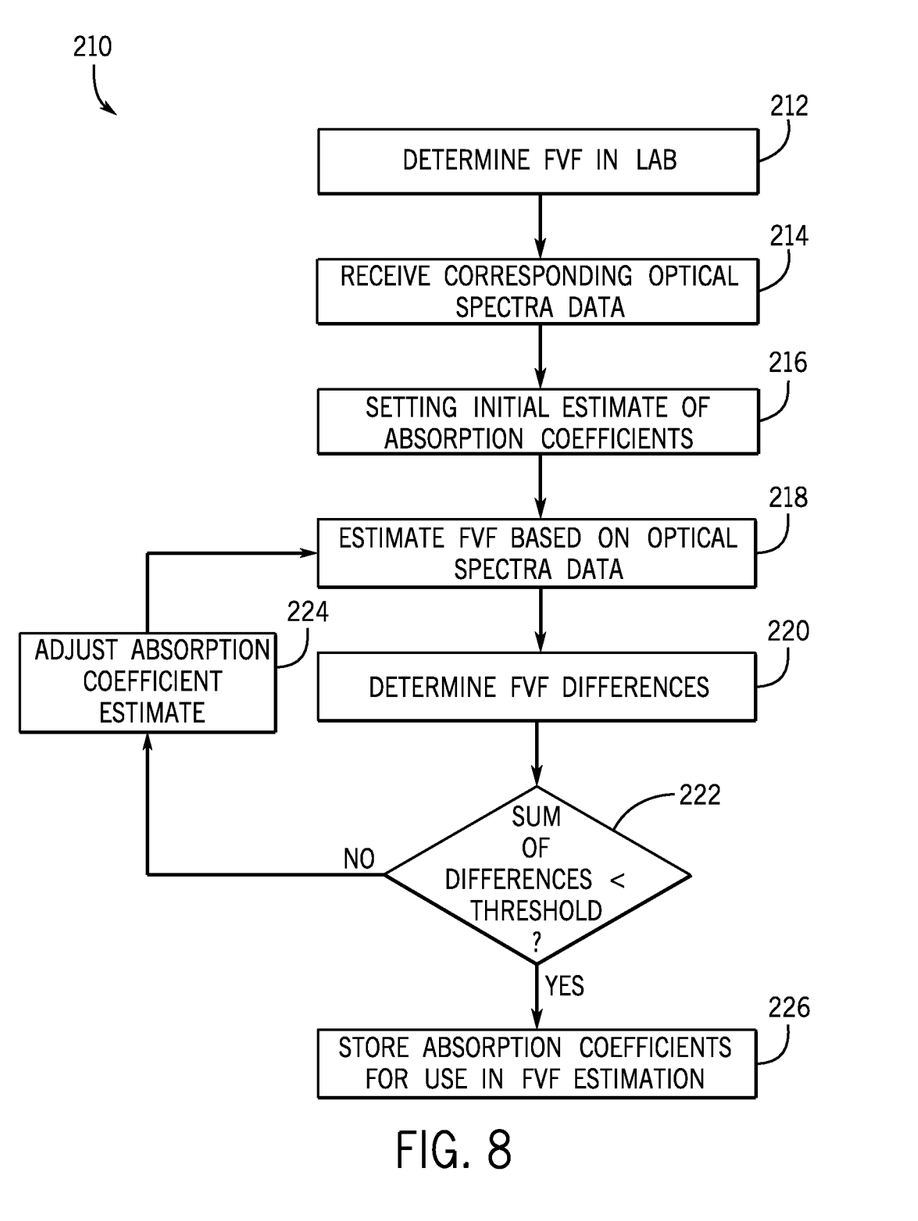
FIG. 8 is a process flow diagram of a method for determining a set of absorption coefficients for use in a formation volume factor estimation, in accordance with an embodiment of the present techniques.

As noted above with reference to FIG. 4, the FVF estimation may utilize absorption coefficients (e.g., in equation 15). These absorption coefficients may be constant parameters that are predetermined, stored in the memory 102, and applied during the estimation process. FIG. 8 is a process flow diagram of a method 210 for determining the absorption coefficients used in the estimation process. The method 210 includes determining (block 212) the FVF for a crude oil sample in a laboratory. This determination may involve PVT analysis of the formation fluid sample after it is brought up to the surface. The method 210 also includes receiving (block 214) the corresponding optical spectra data of the formation fluid, as measured downhole via the spectrometer 72 onboard the downhole tool 50. In addition, the method 210 includes setting (block 216) an initial estimate of absorption coefficients for the FVF estimation. The initial estimate may include a set of absorption coefficients corresponding to certain components of the formation fluid, as input by an operator or selected via a processor. Using the initial estimate, the processor (e.g., processor 100) may estimate (block 218) the FVF of the formation fluid based on the optical spectra data in the database.

The estimated and actual FVF values may be compared using a least squares method to establish an optimal set of absorption coefficients. To that end, the method 210 may include determining (block 220) a difference between the actual FVF values determined in the laboratory and the FVF values estimated using an estimation model (e.g., equation 15) with the absorption coefficients. In some embodiments, the differences may be the square of the differences determined over the fluid samples in the database. The sum of the squares of the differences may be determined and compared (block 222) to a threshold value. If the sum of the squares is over the threshold, the method 210 includes adjusting (block 224) the absorption coefficient estimate, and repeating the FVF estimation and sum of differences calculation. When this value is below the threshold, the method 210 may include storing (block 226) the absorption coefficients in the memory 102 for use in downhole FVF estimations. The absorption coefficients may be optimized to yield relatively accurate prediction results within database spectra measured at various temperatures and pressures. These optimized absorption coefficients are sample independent, but wavelength dependent. Thus, a different set of absorption coefficients may be determined for each wavelength used in the FVF estimation.

It should be noted that the estimation of FVF may be calculated using equation 15 or a similar relationship. In these equations, the estimated FVF value may be different at different wavelengths. That is, respective values for the live oil spectrum and the STO spectrum are input for a single wavelength of the respective optical spectra. To perform the estimation, absorption coefficients are selected for the same wavelength. That is, the estimation of FVF is wavelength dependent. One or more FVF estimates may be determined based on optical spectra data at different wavelengths near the NIR absorption peak. In some embodiments, the FVF estimate may be an average of multiple FVF values, determined at different wavelengths and using the same set of optical spectra data.

Experimental tests have been performed using the presently disclosed FVF estimation techniques. Specifically, 127 samples of optical spectra data of 19 different crude oils were measured at a range of pressures and temperatures. The pressures ranged between 5000 psi and 20000 psi, and the temperatures ranged between 75° C. and 175° C. The actual FVF was measured in a laboratory as well. For each data sample, the same STO spectrum was used, this STO spectrum being an average of the de-colored and de-scattered stock tank optical spectra (FIG. 7). The FVF estimation was performed for each data sample at 6 different wavelengths in the near-infrared region. The estimated FVF and the actual FVF values were compared, and the standard deviation was calculated for each wavelength used in the estimation. These standard deviations are shown below:

| | Wavelength | | | | | |
|---|---|---|---|---|---|---|
| | 1650 nm | 1671 nm | 1690 nm | 1725 nm | 1760 nm | 1800 nm |
| STD | 8.5% | 8.9% | 4.7% | 2.3% | 4.5% | 5.3% |

As shown, the estimations at each wavelength yielded relatively accurate FVF results. Thus, the presently disclosed techniques may provide a reliable measure of FVF in a reduced amount of time, based on the optical spectra data received via the spectrometer 72 of the downhole tool 50. The FVF estimations using the 1725 nm wavelength values of live oil spectrum, STO spectrum, and absorption coefficients yielded a closer agreement with the laboratory data than the other wavelengths. Therefore, it may be desirable to determine the FVF estimation using spectra and coefficient values corresponding to a wavelength within a range of approximately 1700-1740 nm, or approximately 1725 nm.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

What is claimed is:

1. A system, comprising:
a downhole formation fluid sampling tool configured for operation in a downhole environment;
an optical spectrometer of the downhole formation fluid sampling tool, wherein the optical spectrometer is configured to measure an optical characteristic of a formation fluid flowing through the downhole formation fluid sampling tool over a plurality of wavelengths and configured to generate optical spectra data indicative of the optical characteristic; and
a processor, configured to receive the optical spectra data generated by the optical spectrometer, identify respective absorption coefficients for multiple components of the formation fluid, and to estimate a formation volume factor of the formation fluid based on the optical spectra data and the respective absorption coefficients.

2. The system of claim 1, wherein the processor is configured to estimate a composition of the formation fluid based on the optical spectra data and to estimate the formation volume factor based on the estimated composition.

3. The system of claim 2, wherein the processor is configured to estimate respective vapor fractions for multiple components of the formation fluid based on the estimated composition and to estimate the formation volume factor based on the estimated respective vapor fractions of the multiple components.

4. The system of claim 3, wherein the processor is configured to estimate the respective vapor fractions for the multiple components by applying an artificial neural network (ANN) based model to the estimated composition.

5. The system of claim 1, wherein the processor is configured to remove color and scattering from the optical spectra data to generate de-colored optical spectra data and to estimate the formation volume factor based on the de-colored optical spectra data.

6. The system of claim 1, wherein the respective absorption coefficients are predetermined constants derived by applying an optimization algorithm to a database, wherein the database comprises prior optical spectra data and corresponding formation volume factor data.

7. The system of claim 1, wherein the processor is configured to estimate the formation volume factor based on formation fluid parameters and predetermined coefficients corresponding to a single wavelength of the optical spectra data.

8. The system of claim 7, wherein the single wavelength is approximately 1725 nm.

9. The system of claim 1, wherein the optical characteristic comprises an optical density of the formation fluid over a plurality of wavelengths.

10. The system of claim 1, wherein the downhole formation fluid sampling tool is disposed within a wellbore extending into a formation, via a wireline or a string of tubulars.

11. The system of claim 1, wherein the processor is configured to estimate the formation volume factor while the formation fluid is flowing through the downhole formation fluid sampling tool.

12. A method, comprising: receiving optical spectra data into a processor, the optical spectra data being representative of optical characteristics of a formation fluid flowing through a downhole formation fluid sampling tool; identifying, via the processor, respective absorption coefficients for multiple components of the formation fluid; and estimating, via the processor, a formation volume factor of the formation fluid based on the optical spectra data and the respective absorption coefficients, wherein the formation fluid data comprises optical spectra data representative of an optical characteristic of the formation fluid, the optical characteristic being measured via a spectrometer onboard the downhole formation fluid sampling tool.

13. The method of claim 12, comprising determining a fluid type corresponding to the formation fluid based on the optical spectra data, and estimating the formation volume factor of the formation fluid when the formation fluid is determined to be a crude oil.

14. The method of claim 12, wherein estimating the formation volume factor comprises:
removing color and scattering from the optical spectra data to generate de-colored and de-scattered optical spectra data;
estimating a composition of the formation fluid based on the optical spectra data; and
estimating the formation volume factor based on the de-colored and de-scattered optical spectra data and the estimated composition.

15. The method of claim 14, comprising estimating respective vapor fractions of multiple components of the formation fluid based on the estimated composition, and estimating the formation volume factor based on the estimated vapor fractions.

16. The method of claim 12, comprising:
estimating a de-colored and de-scattered stock tank oil spectrum of the formation fluid by determining a spectral offset and coloring present in stock tank optical spectra data, and removing the spectral offset and the coloring from the stock tank optical spectra data to generate the de-colored and de-scattered stock tank oil spectrum; and
estimating the formation volume factor based on the estimated stock tank oil spectrum.

17. The method of claim 16, wherein estimating the stock tank oil spectrum of the formation fluid comprises averaging predetermined stock tank oil spectra corresponding to prior samples of the formation fluid at a stock tank oil condition.

18. A method, comprising: receiving formation fluid data into a processor, the formation fluid data being representative of characteristics of a formation fluid flowing through a downhole formation fluid sampling tool; identifying, via the processor, respective absorption coefficients for multiple components of the formation fluid: and estimating, via the processor, a formation volume factor of the formation fluid based on the formation fluid data and the respective absorption coefficients while the downhole formation fluid sampling tool is disposed within a wellbore extending into a formation, wherein the formation fluid data comprises optical spectra data representative of an optical characteristic of the formation fluid, the optical characteristic being measured via a spectrometer onboard the downhole formation fluid sampling tool.

* * * * *